United States Patent [19]
Tobolski et al.

[11] Patent Number: 5,177,999
[45] Date of Patent: Jan. 12, 1993

[54] MICROHARDNESS TESTER

[75] Inventors: Edward L. Tobolski, Owego; Thomas P. Farrell, Sr.; Giacinto Vallone, both of Endicott, all of N.Y.

[73] Assignee: Wilson Instruments Inc., Binghamton, N.Y.

[21] Appl. No.: 833,814

[22] Filed: Feb. 10, 1992

Related U.S. Application Data

[63] Continuation of Ser. No. 701,303, May 13, 1991, abandoned, which is a continuation of Ser. No. 501,162, Mar. 29, 1990, abandoned.

[51] Int. Cl.$^5$ ............................................. G01N 3/42
[52] U.S. Cl. ......................................................... 73/82
[58] Field of Search ...................................... 73/81-83, 73/85, 852, 853, 856; 356/378; 74/724

[56] References Cited

U.S. PATENT DOCUMENTS

| | | | |
|---|---|---|---|
| 2,376,155 | 5/1945 | Kratzer | 73/81 |
| 2,422,634 | 6/1947 | Riepert et al. | 73/81 |
| 2,674,706 | 4/1954 | Knosp et al. | 74/724 |
| 2,699,540 | 1/1955 | Hunter | 73/81 |
| 2,938,377 | 5/1960 | Sklar | 73/85 |
| 3,200,640 | 8/1965 | Ernst | 73/81 |
| 4,286,479 | 9/1981 | Baumann et al. | 74/724 |
| 4,331,026 | 5/1982 | Howard et al. | 73/81 |
| 4,611,487 | 9/1986 | Krenn et al. | 73/81 |
| 4,621,523 | 11/1986 | Shabel et al. | 73/81 |

FOREIGN PATENT DOCUMENTS 0603531 12/1932 Fed. Rep. of Germany .......... 73/81

OTHER PUBLICATIONS

Wilson Brochure, Tukon Series 200 Microhardness Tester, Binghamton, N.Y.

*Primary Examiner*—Robert Raevis
*Attorney, Agent, or Firm*—Levisohn, Lerner & Berger

[57] ABSTRACT

A microhardness tester comprises a turret capable of holding a plurality of load rod assemblies such that, when the optical objective elements mounted on the turret have been properly aligned with respect to the indenter of one load rod assembly desired to impinge upon a specimen to test for microhardness and it subsequently becomes desirable to use a second load rod assembly to change scales for the testing, it is only necessary to properly align the indenter of the second load rod assembly and not the objective elements with the test specimen. The load rod assembly of the microhardness tester free falls in its testing mode, and a spring is provided for retaining the load rod in a home position spaced away from the test specimen. Thus, the load weights applied to the load rod as carried to the test specimen are not affected by spring load tolerances such that weight calibration can be completed during the weight manufacturing process. Likewise, the weight stack constituting the additional load is guided on a vertical shaft impinging on the load rod so as to provide for actual weights without the need for calibrating spring gradients. The load rod assembly can also be removed from a tester without the necessity of internal disconnection. A threaded anti-rotation collar provides for easy adjustment of the gap between the load rod assembly indenter and the test specimen. The microhardness tester also comprises an elevating unit having a sprocket arrangement providing a rapid focus feature for moving a test specimen into the desired fine focus in minimal time. Still further, a standard dwell time is provided for the tester, with such dwell time factory preset.

9 Claims, 3 Drawing Sheets

MICROHARDNESS TESTER

This is a file wrapper continuation application of application Ser. No. 07/701,303, filed May 13, 1990, now abandoned, which is a continuation of Ser. No. 501,162, filed Mar. 29, 1990 now abandoned.

BACKGROUND OF THE INVENTION

The present invention relates to a microhardness tester of the load rod assembly type.

Prior art load rod assemblies comprise a load rod to which an indenter is attached for impingement on a specimen to be tested for microhardness. These load rod assemblies have springs attached to the load rod to return the rod to a home position spaced apart from the test specimen. A disadvantage of this arrangement is that the weights applied to the load rod to move it and consequently the indenter onto the testing specimen must be calibrated to compensate for the spring load.

Other disadvantages of prior art load rod assemblies are the need for realigning optical objective elements when the indenters are changed to accommodate a new test scale and the relatively long amount of time required to achieve the necessary fine focus on the test specimen when only a single focus control is used. Additionally, there are standard test specifications which operators avoid in their hurry to complete certain tests.

OBJECTS AND SUMMARY OF THE INVENTION

An object of the invention to provide a load rod assembly wherein the loads applied to the load rod are not affected by spring load tolerances so that weight calibration can be completed during the load rod manufacturing process.

Another object of the invention is to eliminate the need for realignment of the objectives when changing test scales.

Another object of the invention is to provide for rapid focusing on the test specimen so as to enable the test specimen or test specimens to be moved any distance more quickly and also to reduce operator fatigue when performing the focusing operation.

Yet another object of the invention is to provide for removal of the load rod assembly from the test apparatus in a simplified manner without the need for internal disconnections.

A further object of the invention is to provide for easy adjustment of the gap between the indenter and the test specimen.

Another object is to provide a standard dwell time test which can not be altered by the operator.

These and other objects of the invention are achieved by the load rod assembly of the present invention wherein a load actuator moves a sleeve downward, depressing a retaining spring which holds the load rod in a home position. As the sleeve moves downward, the restraint on a load rod cap is removed, and the load rod is free to move downward and apply the load to the specimen. Additional weights can be applied to the load rod cap which impinges on the load rod and thus transmits the weight to the test specimen when the load rod moves downward such that the indenter impinges upon the test specimen. For purposes of understanding, the actual distances involved are quite small with total indenter movement generally limited to less than 0.050 inches.

An additional feature of the invention is that the gap between the indenter and the test specimen is easily adjusted by rotating the load rod in a threaded anti-rotation collar. This rotation of the load rod raises or lowers the indenter as desired.

Still another feature of the invention comprises the easy removal of the load rod assembly from a tester by removing retaining screws and a retaining ring and then pulling the load rod assembly downward to remove it from the turret of the tester. Thus, no internal disconnections are required to remove the load rod assembly from the tester.

Another important feature of the invention is the reduction of focus time achieved by having both rapid focus and fine focus control. In both of these controls a worm gear rotates an elevating screw raising or lowering a lift shaft the desired distance. However, the rapid focus control has a greater sprocket ratio than the fine focus control, thus resulting in fewer turns of the rapid focus control driver sprocket to rotate the worm gear. As stated previously, this feature results in the ability to achieve a desired focus on the test specimen in less time and also a reduction in fatigue of the operator attempting to achieve the desired fine focus.

In one of the preferred embodiments of the invention, multiple load rod assemblies are mounted in a single turret. This arrangement gives the advantage that, once the optical objective elements are aligned to the indenter of a first load rod assembly, the subsequent use of a second load rod assembly is facilitated because, instead of the objectives having to be realigned, the indenter of the second load rod assembly is simply aligned to the already aligned objective elements. Such use of multiple indenters on the turret allows for the turret to carry both Knoop and Vickers indenters.

Other features provided relate to the provision of means to prevent non-standard tests from being performed as well as improved means to measure the movement of the indenter.

DESCRIPTION OF THE PREFERRED EMBODIMENTS

Figure 1:
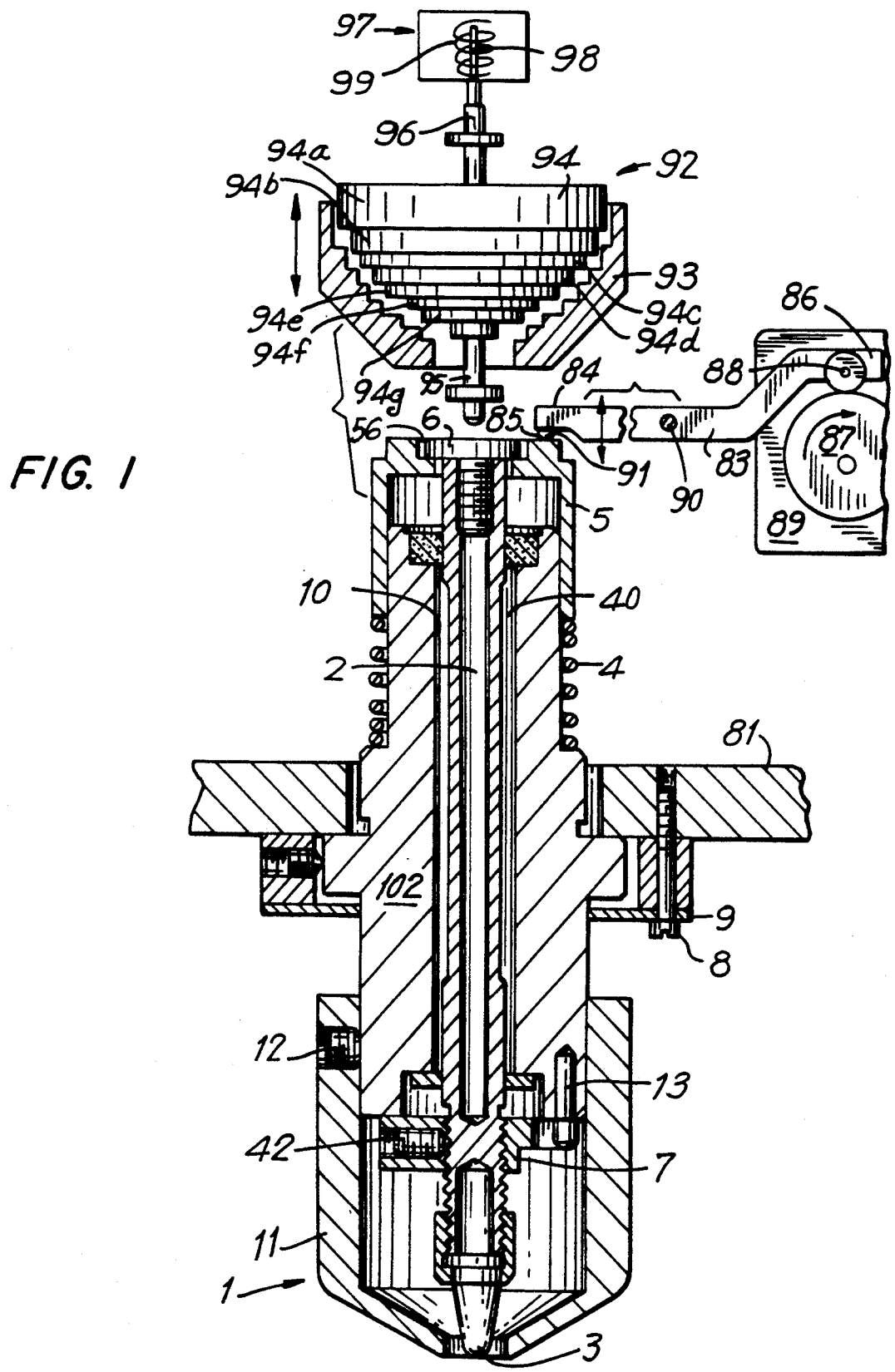
FIG. 1 is an elevational sectional view of the load rod assembly of the present invention.

As shown in FIG. 1, a load rod assembly 1 comprises a load rod 2 which impinges on an indenter 3. The load rod and indentor assembly is held in a home position spaced away from a specimen by the combination of an annular retaining spring 4, a sleeve 5, and a load rod cap 6. One end of sleeve 5 bears on one end of spring 4 while the other end of spring 4 bears on the housing or body element 102 of the load rod and assembly. The upper end of sleeve 5 terminates in a seating surface 56 in which load rod cap 6 is seated. When the sleeve 5 moves upwardly, it carries load rod cap 6 and load rod 2 upwardly. When the sleeve 5 moves downwardly, the load rod 2 is freed to move downwardly by gravity pull.

A load actuator assembly is provided. The load actuator comprises an arm 83, one end 84 of which is located above the upper edge 85 of sleeve 5, while the other end 86 is controlled by a cam 87 moving a cam follower 88 under control of a motor 89. The arm 83 pivots about pivot point 90, and said one end 84 terminates in fingers 91 which bear on said upper edge. When motor 89 is actuated, 86 of arm 84 is moved upwardly causing fingers 91 to push down sleeve 5, freeing the load rod to move downwardly.

A variable load weight assembly 92 is provided which bears on load rod cap 6. A stepped weight lift cone 93 is complementary in shape to a variable load weight assembly 94 with each step on the cone adapted to receive a different weight 94a–94g which controls the amount of additional weight loaded onto load rod cap 6 by bearing rod 95. The variable weights are manually adjusted to cause increasing weights to get into corresponding recesses in weight lifting cone 93.

An upper weight rod 96 is located on top of variable weight assembly and is connected to operate a linear voltage differential transformer 97. After the weight assembly 92 is adjusted to the desired load and bears on load rod cap 6, the measurement process commences by activating motor 89 moving fingers 91 freeing the load rod 2 to move downwardly under the influence of gravity.

Since indenter movement generally does not exceed 0.050 inches, the desired sleeve 5 movement is easy to achieve.

The above arrangement provides the advantage that the loads are not affected by the spring load tolerance of retaining spring 4 so that weight calibration of the variable weight assembly 92 and weights 94a–g can be completed during the weight manufacturing process. In contrast, the prior art load rod assemblies have springs directly attached to the load rod to return it to the home position after testing. As a result, when adjustable weights are used, the weights must be calibrated to compensate for the spring load. After the test is complete in the present device, the spring 4 returns the load rod 2 to its home position since sleeve 5 bears against load rod cap 6, raising it to its original position.

The gap between the indenter 3 and the specimen to be tested for microhardness is adjusted by rotating the load rod 2 in a threaded anti-rotation collar 7. Thus, the gap between the indenter and the test specimen is easily adjusted to the focal point of the objectives. This is accomplished by adjusting the indenter position by rotating threaded collar 7 and allowing pin 13 to fix collar 7 to body 102. A set screw 42 located opposite to pin 13 bears against load rod 2 and is set to prevent rotation of the rod with respect to the collar. This prevents the indenter from rotating during the test.

Load rod assembly removal from the tester is simplified because the only elements needed to effect such removal are retaining screws 8 which hold retaining ring 9 against the housing 81 of the load rod. When these screws are uncoupled from the housing the load rod assembly 1 is removed therefrom.

Load rod 2 moves within a sleeve 10 with sleeve bearings 40 of low friction held therebetween. Sleeve 10 is carried within a protective frustoconical body element 11 at the lower end of sleeve 10, which is connected to body element 102 by screw 12. Screw 42 holds anti-rotation collar 7 to load rod 2.

A measuring device such as an LVDT 97 (linear variable differential transformer) is used to measure indent depth. The LVDT is sensitive to the travel of a magnetic element 98 within a coil 99 with element 98 moved by upper weight rod 96 to identify the amount of movement of the indenter.

Figure 2:
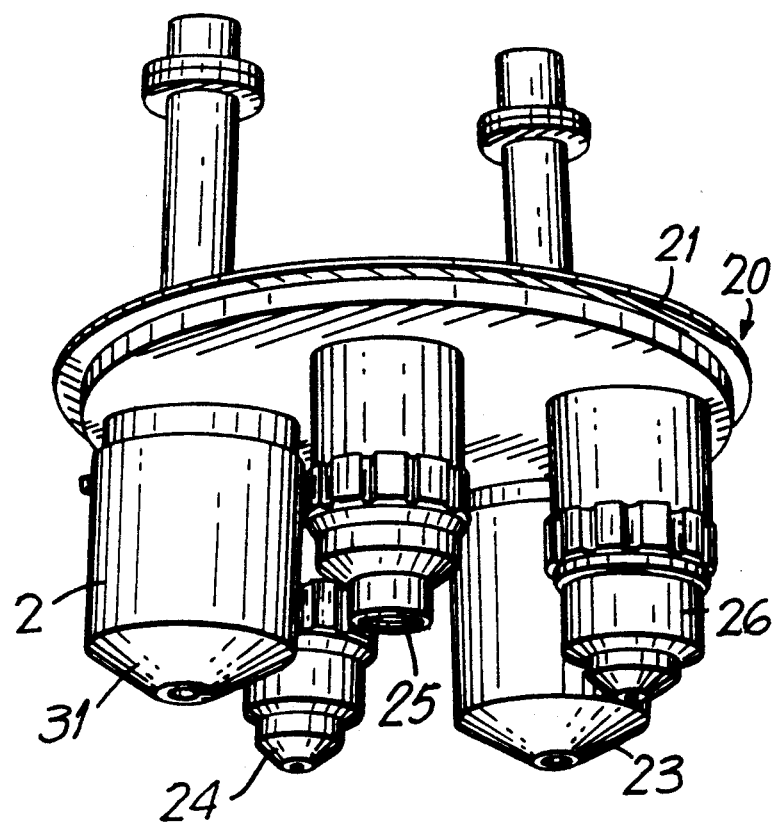
FIG. 2 is a perspective view of a preferred embodiment of the invention wherein multiple load rod assemblies are used in a single turret.

FIG. 2 shows another preferred embodiment of the invention wherein a multiplicity 20 of the load rod assemblies, which might be of the type shown in FIG. 1, are assembled in a single turret. In this embodiment, optical objectives 24, 25 and 26 mounted in turret 21 are aligned to the indenters of the respective load rod assemblies desired to be used. Typically these objectives provide magnifications of 10, 20 and 50x. When another load rod assembly is used, turret 21 is rotated to the operating position under the load actuator (not shown), and the loads are applied as described in connection with FIG. 1. The advantage of this embodiment is that measuring scales (indenters) can be changed without affecting the load application and without having to realign the optical objectives for each change.

Figure 3:
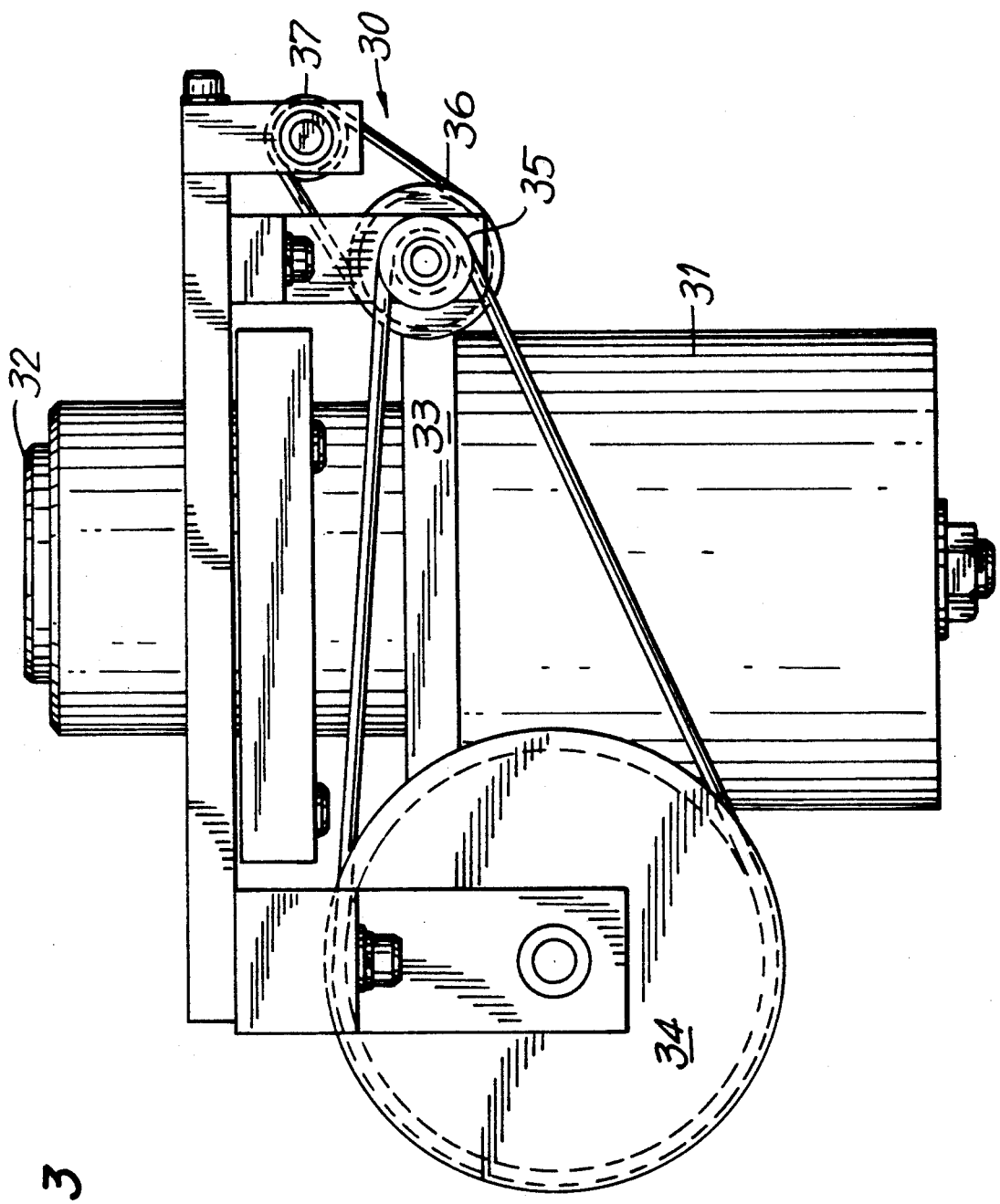
FIG. 3 is a sectional elevational drawing of an elevating unit with a rapid focus feature for moving a testing specimen into proper focus with the objective alignment elements mounted in the turret with the load rod assembly.

The elevating unit of FIG. 3 moves the specimen to be tested for microhardness into proper focus with the objective alignment elements connected in the turret with the load rod assembly. A lift rod 30 comprises a body 31 through which a lift shaft 32 moves to change the position of the testing specimen (not shown). The lift shaft 32 is coupled to a worm gear 33 which is coupled to an elevating screw (not shown) in the conventional manner, thus raising or lowering the lift shaft 32 by the desired distance.

The rapid focus feature is achieved because the combination of a rapid focus sprocket driver 34 manually driven and a driven rapid focus sprocket 35 has a greater sprocket ratio than the fine focus sprocket driver 37 and the driven fine focus sprocket 36. This results in fewer turns of the rapid focus driver sprocket being required to rotate the worm gear 33. As heretofore stated, the advantages of the rapid focus feature are the ability to move the test specimen long distances more quickly and reduces operator fatigue in attaining the required fine focus.

Figure 4:
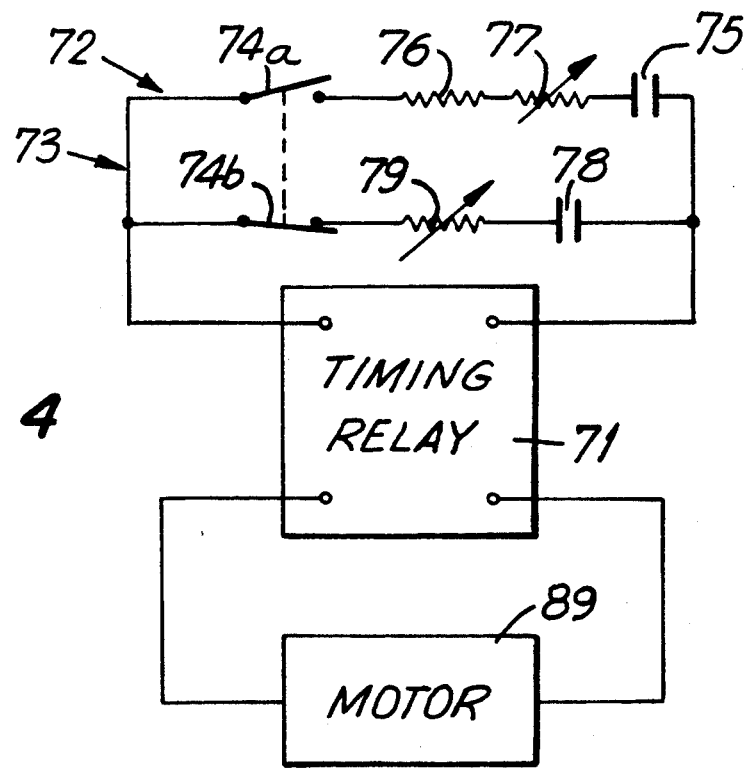
FIG. 4 is a schematic drawing of a standard test dwell time circuit.

FIG. 4 is a schematic diagram of another feature of this invention. ASTM specifications require certain set dwell times for tests to be properly conducted. The present apparatus includes a standard test button accessible to the operator which when actuated engages a timing circuit comprising timing elements which are factory set. In particular the operation of motor 89 is connected to and controlled by a timing relay 71. The input to relay 71, includes among other parameters (not shown) two dwell time control circuits 72 and 73. These are in parallel to each other but only one is connected to the relay 71 at a time due to ganged switches 74a and 74b. Control circuit 72 is operated when a standard dwell time is to be utilized. Capacitor 75 is connected to fixed resistor 76 and variable resistor 77 is factory set. When the standard dwell time is to be used, the operator activates such a switch on the front panel, and the dwell time of the motor is fixed. During normal operation, switch 74b is closed and 74a is open thus connecting variable dwell time circuit 73 to control timing relay 71. This includes a capacitor 78 and a variable resistor 79 controlled by the operator. The timing relay shuts down the motor during the dwell period and reengages it after the dwell time to lift the indentor 3 from the sample. This preset dwell time feature prevents operators from hurrying through their testing procedures.

Although preferred embodiments of the invention have been shown herein, numerous other embodiments within the scope of the appended claims will be readily apparent to those skilled in the art.

What is claimed is:

1. A microhardness tester for performing microhardness measurements using a plurality of respective indenters to conduct microhardness tests in different scales on different specimens, each indenter carried in a respective separate load rod assembly on a rotatable turret to enable said indenters to perform said different microhardness measurements, said microhardness tester comprising:

a rotatable turret having mounted therein at least two separate load rod assemblies directed from said turret toward said test specimen, each load rod assembly having a respective indenter which is moved to perform a respective microhardness measurement on said respective test specimens, a load used in common for actuating any of said each load rod assemblies when said load rod assembly is in position to test in its respective scales, said load rod operated with said each load rod assembly is in position to test in its respective scale, said different test specimens being tested in the same operating position with respect to said turret;

said rotatable turret further having mounted thereon at least one optical objective element directed from said turret toward the test specimen being measured to observe the microhardness test performed and make suitable measurements;

said optical objective element being alignable to observe the test performed by said respective indenter moved by the respective load rod assembly mounted on said turret;

said turret being rotatable to enable each respective indenter to perform a respective microhardness test on said test specimens and to enable said optical objective element to observe each of said respective tests without having changed said operating position.

2. A microhardness tester as set forth in claim 1, further comprising at least two optical objective elements, each having different power magnifications to observe the microhardness tests, said at least two optical objective elements being mounted on said turret to observe the microhardness tests performed by said different indenters.

3. The microhardness tester of claim 1 wherein each of said load rod assemblies comprises a load rod, said indenter connected to a first end of said load rod and functioning to contact said specimen during microhardness testing, an annular spring holding said load rod in a home position spaced away from said test specimen, a sleeve having one end bearing on said spring and the other end supporting a load rod cap, said load rod cap providing a support surface on which an applied weight may be loaded, a load actuator initiating the testing by moving said sleeve downwardly to release said load rod to move downwardly from said home position to move said indenter to contact said test specimen located beneath said indenter; said spring returning said load rod to its home position after the test is complete.

4. The microhardness tester of claim 3 said tester comprising a housing wherein at least one of said plurality of load rod assemblies further comprises a retaining screw connected to said turret to hold a retaining ring against the housing of said tester, said retaining ring holding said at least one load rod assembly to be against said turret.

5. The microhardness tester of claim 3, further comprising adjustable load weight means to adjust the load applied to one of said load rod assemblies for testing.

6. The microhardness tester of claim 3 wherein said microhardness tester comprises a housing, a shaft movable through said housing for moving said specimen to a desired focus position, a worm gear for raising or lowering said shaft, rapid focus means coupled to said worm gear and fine focus means coupled to said worm gear for selectively moving said shaft.

7. A microhardness tester of claim 1 wherein said unit comprises a housing, a shaft movable through said housing for moving said specimen to a desired focus position, a worm gear for raising or lowering said shaft, rapid focus means coupled to said worm gear and fine focus means coupled to said worm gear for selectively moving said shaft.

8. The microhardness tester of claim 7 wherein said fine focus means comprises a first sprocket gear assembly mounted on said housing, and said rapid focus means comprises a second sprocket gear assembly mounted on said housing, said second gear assembly having a greater sprocket ratio than said first sprocket gear assembly so as to rotate said worm gear more rapidly than said first sprocket gear assembly.

9. The microhardness tester of claim 1, further comprising adjustable load weight means to adjust the load applied to one of said load rod assemblies for testing.

* * * * *